US005807993A

United States Patent [19]
French et al.

[11] Patent Number: 5,807,993
[45] Date of Patent: Sep. 15, 1998

[54] HP-8 AUTOANTIGEN

[75] Inventors: Cynthia K. French, Irvine; Karen K. Yamamoto, Los Angeles; Phoebe M. Chow, Temple City; Negemias T. Alido, Chino Hills, all of Calif.

[73] Assignee: VivoRx Autoimmune, Inc., Santa Monica, Calif.

[21] Appl. No.: 421,661

[22] Filed: Apr. 12, 1995

Related U.S. Application Data

[63] Continuation-in-part of Ser. No. 316,068, Sep. 30, 1994, abandoned, which is a continuation of Ser. No. 33,120, Mar. 18, 1993, abandoned.

[51] Int. Cl.[6] .............................. C07K 14/00; C07K 5/00; C07K 2/00; C12N 15/00
[52] U.S. Cl. .......................... 530/350; 530/300; 530/324; 530/358; 435/172.3
[58] Field of Search .................................... 530/350, 300, 530/324, 358; 435/172.3

[56] References Cited

U.S. PATENT DOCUMENTS 4,812,397   3/1989   Weisbart .

FOREIGN PATENT DOCUMENTS 8909273   10/1989   WIPO ............................ C12N 15/00
9421669    9/1994   WIPO .............................. C07K 3/12

OTHER PUBLICATIONS

Zack et al. 1995. J. Immunol. 154(4): 1987–94.
Lieu et al. 1988. J. Clin. Invest. 82: 96–101.
Reeves et al. 1989. JBC 264(9): 5047–52.
Ben–Chetrit. et al. 1989. J. Clin. Invest. 83: 1284–1292.
Wagatsuma et al. 1993. Molecular Immunol. 30(16): 1491–98.
Deutscher et al. 1988. PNAS 85: 9479–83.
Okubo et al. 1993. J. Immunol. 151(2): 1108–115.
Bowie et al. 1990. Science 247: 1306–1310.
Cram et al. 1990. J. Immunol. 145(2): 630–635.
Richard H. Weisbart et al., A Conserved Anti–DNA Antibody Idiotype Associated with Nephritis in Murine and Human Systemic Lupus Erythematosus, The Journal of Immunology, vol. 144, 2653–2658, No. 7, Apr. 1, 1990.

Sashko Damjanovski et al., Molecular Analysis of *Xenopus Laevis* Sparc (Secreted Protein Acidic, Rich in Cysteine), Biochem. J., vol. 281, 513–517, (1992).

John H. McVey et al., Characterization of the Mouse Sparc/Osteonectin Gene, The Journal of Biological Chemistry, vol. 263, No. 23, pp. 11111–11116, Aug. 15, 1988.

Jurgen Engel et al., Calcium Binding Domains and Calcium–Induced Conformational Transition of SPARC/BM–40/Osteonectin, An Extracellular Glycoprotein Expressed in Mineralized and Nonmineralized Tissues, Biochemistry 1987, 26, 6958–6965.

Ian G. Johnston et al., Molecular Cloning of SC1: A Putative Brain Extracellular Matrix Glycoprotein Showing Partial Similarity to Osteonectin/BM40/SPARC, Neuron, vol. 2, 165–176, Jan. 1990.

A.J.G. Swaak and R. Smeenk, Clinical Differences Between S.L.E. Patients in Relation to the Avidity of Their Anti–DS DNA.

Peter H. Schur, Third International Conference on Systemic Lupus Erythematosus, Arthritis and Rheumatism, vol. 35, No. 10, pp. 1238–1240 (Oct. 1992).

Russell P. Tracy et al., Minireview—The Osteonectin Family of Proteins, J. Biochem, vol. 20, No. 7, pp. 653–660, 1988.

Theissen et al, EMBO Journal, 5(12):3209–3217, 1986.

Okubo et al, J. Immunology 153;3784–3790, 1994.

Okubo et al, Arth. & Rheum., 35(9) Suppl: S39 Abstract #29, 1992.

*Primary Examiner*—N. M. Minnifield
*Attorney, Agent, or Firm*—Stephen E. Reiter; Gray Cary Ware & Freidenrich

[57]  ABSTRACT

An autoantigen identified as HP-8 which is related to systemic lupus erythematosus. The HP-8 antigen is expressed by a gene which was identified by immunoscreening of human placental cDNA GT11 expression library with the monoclonal antibody 3E10. The 3E10 antibody is a low-affinity anti-double-stranded DNA autoantibody derived from the MRL murine models for human systemic lupus erythematosus.

4 Claims, 9 Drawing Sheets

FIGURE 1

```
 1   CAACTTCAATTTTCTGCAGTGGCTCTGgGTCCAGCCCCTTaCTTAAAGATCTGGAAAGCATGAAGACT    69
     GTTGAAGTTAAAAAGACGTCACCGAGACCCAGGTCGGGAAtGAATTTCTAGACCTTTCGTACTTCTGA
     ③→                                                      METLysThr

70  GGGCTTTTTTCCTATGTCTCTTGGGAACTGCAGCTGCAATCCCGACAAATGCAAGATTATTATCTGAT   138
     CCCGAAAAAAGGATACAGAGAACCCTTGACGTCGACGTGTTAGGGCTGTTTACGTTCTAATAATAGACTA
     GlyLeuPhePheLeuCyaLeuLeuGlyThrAlaAlaIleProThrAsnAlaArgLeuLeuSerAsp

139  CATTCCAAACCAACTGCTGAAACGGTAGCACCCGACAACACTGCAATCCCCAGTTTAAGGGCTGAAGaT   207
     GTAAGGTTTGGTTGACGACTTTGCCATCGTGGGCTGTTGTGACGTTAGGGGTCAAATTCCCGACTTCTA
     HisSerLysProThrAlaGluThrAlaProAspAsnThrAlaIleProSerLeuArgAlaGluAsp

208  GAAGAAAAATGAAAAAGAGGAAAACAGCAGTATCCACAgAAGACGATTCCCACCATAAGGCTGAAAAATCATCA   276
     CTTCTTTTTACTTTTTCTCTTTGTCGTCATAGGTGTCTTCTGCTAAGGGTGGTATTCCGACTTTTTAGTAGT
     GluGluAsnGluLysGluThrAlaValSerThrGluAspAspSerHisLysAlaGluLysSerSer
                        ②→

277  GTACTAAAGTCAAAAGAGGAAAGCCATGAACAGtCAGCAGAACAGGGCAAGAGTTCTAgCCAAGAGCTG   345
     CATGATTTCAGTTTTCTCCTTTCGGTACTTGTCAGTCGTCTTGTCCCGTTCTCAAGATCGGTTCTCGAC
     ValLeuLysSerHisGluSerHisGluGlnGlySerAlaGluGlnSerSerSerGlnGluLeu
```

```
691  GTTGGTACCCACAATGATAACCAAGAAAGACAGAATTGCCAGGAGCATGCTAACAGCAAGCAG  759
     CAACCATGGGTGTTACTATTGGTTCTTTCTGTCTTAACGGTCCCTCGTACGATTGTCGTTCGTC
     ValGlyThrHisAsnAspAsnGlnGluArgLysThrGluLeuProArgGluHisAlaAsnSerLysGln

760  GAGGAAGACAATACCCAATCTGATGATATTTGGAAGAGTCTGATCAACCAACTCAAGTAAGCAAGATG  828
     CTCCTTCTGTTATGGGTTAGACTACTATAAAACCTTCTCAGACTAGTTGGTTGAGTTCATTCGTTCTAC
     GluGluAspAsnThrGlnSerAspAspIleLeuGluSerAspGlnProThrGlnValSerLysMET

829  CAGGAGGATGAATTTGATCAGGGTAACCAAGAACAAGAGATAACTCCAATGCAGAAATGGAAGAGGAA  897
     GTCCTCCTACTTAAACTAGTCCCATTGGTTCTTGTTCTCTATTGAGGTTACGTCTTTACCTTCTCCTT
     GlnGluAspGluPheAspGlnGlyAsnGlnGluGlnGluAspAsnSerAsnAlaGluMETGluGluGlu

898  AATGCATCGAACGTCAATAAGCACACATTCAAGAAACTGAATGGCAGAGTCAAGAGGTAAAAACTGGCCTA  966
     TTACGTAGCTTGCAGTTATTCGTGTGTAAGTTCTTTGACTTACCGTCTCAGTTCTCCCATTTTGACCGGAT
     AsnAlaSerAsnValAsnLysHisIleGlnAsnLeuAsnGlyArgValLysArgValLysThrGlyLeu

967  GAAGCTATCAGCAACCACAAAGAGACAGAAGAAAAGACTGTTTCTGAGGCTCTGCTCATGGAACCTACT  1035
     CTTCGATAGTCGTTGGTGTTTCTCTGTCTTCTTTTCTGACAAAGACTCCGAGACGAGTACCTTGGATGA
     GluAlaIleSerAsnHisLysGluThrGluGluLysThrValSerGluAlaLeuLeuMETGluProThr
```

Figure 2A-3

1036 GATGATGGTAATACCACGCCCAGAAATCATGGAGTTGATGATGATGGCGATGATGATGGC 1104
     CTACTACCATTATGGTGCGGGTCTTTAGTACCTCAACTACTACTACCGCTACTACTACCG
     AspAspGlyAsnThrThrProArgAsnHisGlyValAspAspAspGlyAspAspAspGly

1105 GGCACTGATGGCCCCAGGCACAGTGCAAGTGATGACTACTTCATCCCAGCCAGGCCTTTCTGGAGCC 1173
     CCGTGACTACCGGGGTCCGTGTCACTTCACTACTGATGAAGTAGGGTTCGGTCCGAAAGACCTCCGG
     GlyThrAspGlyProArgHisSerAlaSerAspAspTyrPheIleProSerGlnAlaPheLeuGluAla

1174 GAGAGAGCTCAATCCATTGCCTATCACCTCAAAATTGAGGAGCAAAGAGAAAAAGTACATGAAAATGAA 1242
     CTCTCTCGAGTTAGGTAACGGATAGTGGAGTTTTAACTCCTCGTTTCTCTTTTCATGTACTTTTACTT
     GluArgAlaGlnSerIleAlaTyrHisLeuLysIleGluGluGlnArgGluLysValHtsGluAsnGlu

1243 AATATAGGTACCACTGAGCCTGGAGAGCACCAAGAGGCCAAGAAGCAGAGAACTCATCAAATGAGGAG 1311
     TTATATCCATGGTGACTCGGACCTCGTCGTGGTTCCGGTTCTTCGTCTCTTGAGTAGTTACTCCTC
     AsnIleGlyThrThrGluProGlyGluHisGlnGluAlaLysLysAlaGluAsnSerSerAsnGluGlu

1312 GAAACGTCAAGTGAAGGCAACATGAGGGTGCATGCTGTGGATTCTTGCATGAGCTTCCAGTGTAAAAGA 1380
     CTTTGCAGTTCACTTCCGTTGTACTCCACGTACGACACCTAAGAACGTACTCGAAGGTCACATTTCT
     GluThrSerSerGluGlyAsnMETArgValHisAlaValAspSerCysMETSerPheGlnCysLysArg

Figure 2A-4

```
1381  GGCCACATCTGTAAGGCAGACCAACAGGGAAAACCTCACTGTGTCTGCCAGGATCCAGTGACTTGTCCT   1449
      CCGGTGTAGACATTCCGTCTGGTTGTCCCTTTTGGAGTGACACAGACGGTCCTAGGTCACTGAACAGGA
      ************************************************************
      GlyHisIleCysLysAlaAspGlnGlyLysProHisCysValCysGlnAspThrCysPro

1450  CCAACAAAACCCCTTGATCAAGTTTGTGGCACTGACAATCAGACCTAGTTCCTGTCATCTATTC        1518
      GGTTGTTTTGGGAACTAGTTCAAACACCGTGACTGTTAGTCTGGATCTGGATACGACCAAGGACAGTAGATAAG
      ************************************************************
      ProThrLysProLeuAspIleLysPheValCysGlyThrAspSerAlaSerCysHisLeuPhe

1519  GCTACTAAATGCAGACTGGAGGGGACCAAAAAGGGGCATCAACTCCAGTCGATTATTTTGGAGCCTGC    1587
      CGATGATTTACGTCTGACCTCCCCTGGTTTTTCCCCGTAGTTGAGGTCGACCTAATAAAACCTCGGACG
      ************************************************************
      AlaThrLysCysArgLeuGluGlyThrLysLysGlyHisGlnLeuGlnLeuAspTyrPheGlyAlaCys

1588  AAATCTATTCCTACTTGTACGGACTTTGAAGTGATTCAGTTTCCTCTACGGATGAGAGACTGGCTCAAG   1656
      TTTAGATAAGGATGAACATGCCTGAAACTTCACTAAGTCAAAGGAGATGCCTACTCTCTGACCGAGTTC
      ************************************************************
      LysSerIleProThrCysThrAspPheGluValIleGlnPheProLeuArgMETArgAspTrpLeuLys

1657  AATATCCTCATGCAGCTTTATGAAGCCAACTCTGAACACGCTGGTTATCTAAATGAGAAGCAGAGAAAT  1725
      TTATAGGAGTACGTCGAAATACTTCGGTTGAGACTTGTGCGACCAATAGATTACTCTTCGTCTCTTTA
      ************************************************************
      AsnIleLeuMETGlnLeuTyrGluAlaAsnSerGluHisAlaGlyTyrLeuAsnGluLysGlnArgAsn
```

Figure 2A-5

1726 AAAGTCAAGAAAATTTACCTGGATGAAAAGAGGCTTTTGGCTGGGGACCATCCCATTGACCTTCTCTTA 1794
     TTTCAGTTCTTTTAAATGGACCTACTTTTCTCCGAAAACCGACCCCTGGTAGGGTAACTGGAAGAGAAT
     LysValLysLysIleTyrLeuAspGluLysArgLeuLeuAlaGlyAspHisProIleAspLeuLeuLeu

1795 AGGGACTTTAAGAAAAACTACCACATGTGTATCCTGTGCACTGGCAGTTTAGTGAACTTGACCAA 1863
     TCCCTGAAATTCTTTTTGATGGTGTACATACAATAGGACACGTGACCGTCAAATCACTTGAACTGGTT
     ArgAspPheLysLysAsnTyrHisMETTyrValTyrProValHisTrpGlnPheSerGluLeuAspGln

1864 CACCCTATGGATAGAGTCTTGACACATTCTGAACTTGCTCCTCTGCGAGCATCTCTGGTGCCCATGGAA 1932
     GTGGGATACCTATCTCAGAGAACTGTAAGACTTGAACGAGGAGACGCTCGTAGAGACCACGGGTACCTT
     HisProMETAspArgValLeuThrHisSerGluLeuAlaProLeuArgAlaSerLeuValProMETGlu

1933 CACTGCATAACCCGTTTCTTTGAGGAGTGTGACCCCAACAAGGATAAGCACATCACCCTGAAGGAGTGG 2001
     GTGACGTATTGGGCAAAGAAACTCCTCACACTGGGGTTGTTCCTATTCGTGTAGTGGGACTTCCTCACC
     HisCysIleThrArgPhePheGluGluCysAspProAsnLysAspLysHisIleThrLeuLysGluTrp

2002 GGCCACTGCTTTGGAATTAAAGAAGAGGACATAGATGAAAAATCTCTTGTTTGAACGAAGATTTAAAG 2070
     CCGGTGACGAAACCTTAATTCTTCTCCTGTATCTACTTTTAGAGAACAAAACTTGCTTCTAAAATTC
     GlyHisCysPheGlyIleLysGluAspIleAspGluAsnLeuLeuPhe

Figure 2A-6

```
2071  AACTCAACTTTCCAGCATCCTCCTCTGTTCTAACCACTTCAGAAATATATGCAGCTGTGATACTTGTAG  2139
      TTGAGTTGAAAGGTCGTAGGAGGAGACAAGATTGGTGAAGTCTTTATATACGTCGACACTATGAACATC

2140  ATTTATATTTAGCAAAATGTTAGCATGTATGACAAGACAATGAGAGTAATTGCTTGACAACAACCTATG  2208
      TAAATATAAATCGTTTTACATACGTACATACTGTTCTGTTACTCTCATTAACGAACTGTTGTTGGATAC

2209  CACCAGGTATTAACATTAACTTTGGAAACAAAAATGTACAATTAAGTAAAGTCAACATATGCAAAATA  2277
      GTGGTCCATAAATTGTAAATTGAAACCTTTGTTTTTACATGTTAATTCATTTCAGTTGTATACGTTTAT

2278  CTGTACACATTGTGAACAGAAGTTTAATTCATAGTAATTTCACTCTCTGCATTGACTTATGAGATAATTAA  2346
      GACATGTAACACTTGTCTTCAAATTAAGTATCATTAAAGTGAGAGACGTAACTGAATACTCTATTAATT

2347  TGATTAAACTATTAATGATAAAAATAATGCATTTGTATTGTTCATAATATCATGTGCACTTCAAGAAAA  2415
      ACTAATTTGATAATTACTATTTTATTACGTAAACATAACAAGTATTATAGTACACGTGAAGTTCTTTT
```

Figure 2A-7

2416 TGGAATGCTACTCTTTGTGGTTTACGTGTATTATTTCAATATCTTAAT 2465
     ACCTTACGATGAGAAAACACCAAATGCACATAATAAAAGTTATAGAATTA

*** denotes original HP8 clone sequence (original patent application)

① denotes 5' end of HFB4-1 clone (sequenced 06/02/93)

② denotes 5' end of RACE clone #9 (sequenced 07/14/93)

③ denotes 5' end of RACE clone #6 (sequenced 08/05/93)

Figure 2A-8

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 154 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( i x ) FEATURE:
( A ) NAME/KEY: CDS
( B ) LOCATION: 2..154

( x i ) SEQUENCE DESCRIPTION: SEQ ID NO:1:

```
G GAA TTC GGG TTT CCC TGT GTC TGC GAG GAT CCA GTG ACT TGT CCT      46
  Glu Phe Gly Phe Pro Cys Val Cys Glu Asp Pro Val Thr Cys Pro
  1               5                   10                  15

CCA ACA AAA CCC CTT GAT CAA GTT TGT GGC ACT GAC AAT CAG ACC TAT    94
Pro Thr Lys Pro Leu Asp Gln Val Cys Gly Thr Asp Asn Gln Thr Tyr
                20                  25                  30

GCT AGT TCC TGT CAT CTA TTC GCT ACT AAA TGC AGA CTG GAG GGG ACC   142
Ala Ser Ser Cys His Leu Phe Ala Thr Lys Cys Arg Leu Glu Gly Thr
            35                  40                  45

AAA AAG GCC CCC                                                   154
Lys Lys Ala Pro
        50
```

( 2 ) INFORMATION FOR SEQ ID NO:2:

( i ) SEQUENCE CHARACTERISTICS:
( A ) LENGTH: 51 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Glu Phe Gly Phe Pro Cys Val Cys Glu Asp Pro Val Thr Cys Pro Pro
1               5                   10                  15

Thr Lys Pro Leu Asp Gln Val Cys Gly Thr Asp Asn Gln Thr Tyr Ala
            20                  25                  30

Ser Ser Cys His Leu Phe Ala Thr Lys Cys Arg Leu Glu Gly Thr Lys
        35                  40                  45
```

Lys Ala Pro
        50

( 2 ) INFORMATION FOR SEQ ID NO:3:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( i x ) FEATURE:
        ( A ) NAME/KEY: CDS
        ( B ) LOCATION: 1..132

( x i ) SEQUENCE DESCRIPTION: SEQ ID NO:3:

```
TGT  GTC  TGC  CAG  GAT  CCA  GTG  ACT  TGT  CCT  CCA  ACA  AAA  CCC  CTT  GAT        48
Cys  Val  Cys  Gln  Asp  Pro  Val  Thr  Cys  Pro  Pro  Thr  Lys  Pro  Leu  Asp
               55                       60                      65

CAA  GTT  TGT  GGC  ACT  GAC  AAT  CAG  ACC  TAT  GCT  AGT  TCC  TGT  CAT  CTA        96
Gln  Val  Cys  Gly  Thr  Asp  Asn  Gln  Thr  Tyr  Ala  Ser  Ser  Cys  His  Leu
          70                       75                      80

TTC  GCT  ACT  AAA  TGC  AGA  CTG  GAG  GGG  ACC  AAA  AAG                          132
Phe  Ala  Thr  Lys  Cys  Arg  Leu  Glu  Gly  Thr  Lys  Lys
          85                  90                  95
```

( 2 ) INFORMATION FOR SEQ ID NO:4:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Cys  Val  Cys  Gln  Asp  Pro  Val  Thr  Cys  Pro  Pro  Thr  Lys  Pro  Leu  Asp
 1                   5                      10                      15

Gln  Val  Cys  Gly  Thr  Asp  Asn  Gln  Thr  Tyr  Ala  Ser  Ser  Cys  His  Leu
               20                       25                      30

Phe  Ala  Thr  Lys  Cys  Arg  Leu  Glu  Gly  Thr  Lys  Lys
               35                       40
```

( 2 ) INFORMATION FOR SEQ ID NO:5:

( i ) SEQUENCE CHARACTERISTICS:
        ( A ) LENGTH: 2465 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens -continued ( i x ) FEATURE:
    ( A ) NAME/KEY: CDS
    ( B ) LOCATION: 61..2054

( x i ) SEQUENCE DESCRIPTION: SEQ ID NO:5:

```
CAACTTCAAT  TTTTCTGCAG  TGGCTCTGGG  TCCAGCCCCT  TACTTAAAGA  TCTGGAAAGC         60

ATG  AAG  ACT  GGG  CTT  TTT  TTC  CTA  TGT  CTC  TTG  GGA  ACT  GCA  GCT  GCA   108
Met  Lys  Thr  Gly  Leu  Phe  Phe  Leu  Cys  Leu  Leu  Gly  Thr  Ala  Ala  Ala
 45                      50                      55                       60

ATC  CCG  ACA  AAT  GCA  AGA  TTA  TTA  TCT  GAT  CAT  TCC  AAA  CCA  ACT  GCT   156
Ile  Pro  Thr  Asn  Ala  Arg  Leu  Leu  Ser  Asp  His  Ser  Lys  Pro  Thr  Ala
                      65                       70                   75

GAA  ACG  GTA  GCA  CCC  GAC  AAC  ACT  GCA  ATC  CCC  AGT  TTA  AGG  GCT  GAA   204
Glu  Thr  Val  Ala  Pro  Asp  Asn  Thr  Ala  Ile  Pro  Ser  Leu  Arg  Ala  Glu
                  80                       85                       90

GAT  GAA  GAA  AAT  GAA  AAA  GAA  ACA  GCA  GTA  TCC  ACA  GAA  GAC  GAT  TCC   252
Asp  Glu  Glu  Asn  Glu  Lys  Glu  Thr  Ala  Val  Ser  Thr  Glu  Asp  Asp  Ser
              95                      100                      105

CAC  CAT  AAG  GCT  GAA  AAA  TCA  TCA  GTA  CTA  AAG  TCA  AAA  GAG  GAA  AGC   300
His  His  Lys  Ala  Glu  Lys  Ser  Ser  Val  Leu  Lys  Ser  Lys  Glu  Glu  Ser
         110                      115                      120

CAT  GAA  CAG  TCA  GCA  GAA  CAG  GGC  AAG  AGT  TCT  AGC  CAA  GAG  CTG  GGA   348
His  Glu  Gln  Ser  Ala  Glu  Gln  Gly  Lys  Ser  Ser  Ser  Gln  Glu  Leu  Gly
125                      130                      135                      140

TTG  AAG  GAT  CAA  GAG  GAC  AGT  GAT  GGT  GAC  TTA  AGT  GTG  AAT  TTG  GAG   396
Leu  Lys  Asp  Gln  Glu  Asp  Ser  Asp  Gly  Asp  Leu  Ser  Val  Asn  Leu  Glu
                      145                      150                      155

TAT  GCA  CCA  ACT  GAA  GGT  ACA  TTG  GAC  ATA  AAA  GAA  GAT  ATG  AGT  GAG   444
Tyr  Ala  Pro  Thr  Glu  Gly  Thr  Leu  Asp  Ile  Lys  Glu  Asp  Met  Ser  Glu
                  160                      165                      170

CCT  CAG  GAG  AAA  AAA  CTC  TCA  GAG  AAC  ACT  GAT  TTT  TTG  GCT  CCT  GGT   492
Pro  Gln  Glu  Lys  Lys  Leu  Ser  Glu  Asn  Thr  Asp  Phe  Leu  Ala  Pro  Gly
              175                      180                      185

GTT  AGT  TCC  TTC  ACA  GAT  TCT  AAC  CAA  CAA  GAA  AGT  ATC  ACA  AAG  AGA   540
Val  Ser  Ser  Phe  Thr  Asp  Ser  Asn  Gln  Gln  Glu  Ser  Ile  Thr  Lys  Arg
         190                      195                      200

GAG  GAA  AAC  CAA  GAA  CAA  CCT  AGA  AAT  TAT  TCA  CAT  CAT  CAG  TTG  AAC   588
Glu  Glu  Asn  Gln  Glu  Gln  Pro  Arg  Asn  Tyr  Ser  His  His  Gln  Leu  Asn
205                      210                      215                      220

AGG  AGC  AGT  AAA  CAT  AGC  CAA  GGC  CTA  AGG  GAT  CAA  GGA  AAC  CAA  GAG   636
Arg  Ser  Ser  Lys  His  Ser  Gln  Gly  Leu  Arg  Asp  Gln  Gly  Asn  Gln  Glu
                      225                      230                      235

CAG  GAT  CCA  AAT  ATT  TCC  AAT  GGA  GAA  GAG  GAA  GAA  GAA  AAA  GAG  CCA   684
Gln  Asp  Pro  Asn  Ile  Ser  Asn  Gly  Glu  Glu  Glu  Glu  Glu  Lys  Glu  Pro
                  240                      245                      250

GGT  GAA  GTT  GGT  ACC  CAC  AAT  GAT  AAC  CAA  GAA  AGA  AAG  ACA  GAA  TTG   732
Gly  Glu  Val  Gly  Thr  His  Asn  Asp  Asn  Gln  Glu  Arg  Lys  Thr  Glu  Leu
              255                      260                      265

CCC  AGG  GAG  CAT  GCT  AAC  AGC  AAG  CAG  GAG  GAA  GAC  AAT  ACC  CAA  TCT   780
Pro  Arg  Glu  His  Ala  Asn  Ser  Lys  Gln  Glu  Glu  Asp  Asn  Thr  Gln  Ser
         270                      275                      280

GAT  GAT  ATT  TTG  GAA  GAG  TCT  GAT  CAA  CCA  ACT  CAA  GTA  AGC  AAG  ATG   828
Asp  Asp  Ile  Leu  Glu  Glu  Ser  Asp  Gln  Pro  Thr  Gln  Val  Ser  Lys  Met
285                      290                      295                      300

CAG  GAG  GAT  GAA  TTT  GAT  CAG  GGT  AAC  CAA  GAA  CAA  GAA  GAT  AAC  TCC   876
Gln  Glu  Asp  Glu  Phe  Asp  Gln  Gly  Asn  Gln  Glu  Gln  Glu  Asp  Asn  Ser
                      305                      310                      315

AAT  GCA  GAA  ATG  GAA  GAG  GAA  AAT  GCA  TCG  AAC  GTC  AAT  AAG  CAC  ATT   924
Asn  Ala  Glu  Met  Glu  Glu  Glu  Asn  Ala  Ser  Asn  Val  Asn  Lys  His  Ile
                  320                      325                      330
```

| | | | | | | | | | | | | | | | | |
|---|---|---|---|---|---|---|---|---|---|---|---|---|---|---|---|---|
| CAA | GAA | ACT | GAA | TGG | CAG | AGT | CAA | GAG | GGT | AAA | ACT | GGC | CTA | GAA | GCT | 972 |
| Gln | Glu | Thr 335 | Glu | Trp | Gln | Ser | Gln 340 | Glu | Gly | Lys | Thr | Gly 345 | Leu | Glu | Ala | |
| ATC | AGC | AAC | CAC | AAA | GAG | ACA | GAA | GAA | AAG | ACT | GTT | TCT | GAG | GCT | CTG | 1020 |
| Ile | Ser | Asn 350 | His | Lys | Glu | Thr | Glu 355 | Glu | Lys | Thr | Val | Ser 360 | Glu | Ala | Leu | |
| CTC | ATG | GAA | CCT | ACT | GAT | GAT | GGT | AAT | ACC | ACG | CCC | AGA | AAT | CAT | GGA | 1068 |
| Leu 365 | Met | Glu | Pro | Thr | Asp 370 | Asp | Gly | Asn | Thr | Thr 375 | Pro | Arg | Asn | His | Gly 380 | |
| GTT | GAT | GAT | GAT | GGC | GAT | GAT | GAT | GGC | GAT | GAT | GGC | GGC | ACT | GAT | GGC | 1116 |
| Val | Asp | Asp | Asp | Gly 385 | Asp | Asp | Asp | Gly 390 | Asp | Asp | Gly | Gly | Thr | Asp | Gly 395 | |
| CCC | AGG | CAC | AGT | GCA | AGT | GAT | CAC | TAC | TTC | ATC | CCA | AGC | CAG | GCC | TTT | 1164 |
| Pro | Arg | His | Ser 400 | Ala | Ser | Asp | His | Tyr 405 | Phe | Ile | Pro | Ser | Gln 410 | Ala | Phe | |
| CTG | GAG | GCC | GAG | AGA | GCT | CAA | TCC | ATT | GCC | TAT | CAC | CTC | AAA | ATT | GAG | 1212 |
| Leu | Glu | Ala | Glu 415 | Arg | Ala | Gln | Ser | Ile 420 | Ala | Tyr | His | Leu | Lys 425 | Ile | Glu | |
| GAG | CAA | AGA | GAA | AAA | GTA | CAT | GAA | AAT | GAA | AAT | ATA | GGT | ACC | ACT | GAG | 1260 |
| Glu | Gln | Arg | Glu 430 | Lys | Val | His | Glu | Asn 435 | Glu | Asn | Ile | Gly | Thr 440 | Thr | Glu | |
| CCT | GGA | GAG | CAC | CAA | GAG | GCC | AAG | AAA | GCA | GAG | AAC | TCA | TCA | AAT | GAG | 1308 |
| Pro 445 | Gly | Glu | His | Gln | Glu 450 | Ala | Lys | Lys | Ala | Glu 455 | Asn | Ser | Ser | Asn | Glu 460 | |
| GAG | GAA | ACG | TCA | AGT | GAA | GGC | AAC | ATG | AGG | GTG | CAT | GCT | GTG | GAT | TCT | 1356 |
| Glu | Glu | Thr | Ser | Ser 465 | Glu | Gly | Asn | Met | Arg 470 | Val | His | Ala | Val | Asp 475 | Ser | |
| TGC | ATG | AGC | TTC | CAG | TGT | AAA | AGA | GGC | CAC | ATC | TGT | AAG | GCA | GAC | CAA | 1404 |
| Cys | Met | Ser | Phe 480 | Gln | Cys | Lys | Arg | His 485 | Ile | Cys | Lys | Ala | Asp 490 | Gln | | |
| CAG | GGA | AAA | CCT | CAC | TGT | GTC | TGC | CAG | GAT | CCA | GTG | ACT | TGT | CCT | CCA | 1452 |
| Gln | Gly | Lys 495 | Pro | His | Cys | Val | Cys 500 | Gln | Asp | Pro | Val | Thr 505 | Cys | Pro | Pro | |
| ACA | AAA | CCC | CTT | GAT | CAA | GTT | TGT | GGC | ACT | GAC | AAT | CAG | ACC | TAT | GCT | 1500 |
| Thr | Lys 510 | Pro | Leu | Asp | Gln | Val 515 | Cys | Gly | Thr | Asp | Asn 520 | Gln | Thr | Tyr | Ala | |
| AGT | TCC | TGT | CAT | CTA | TTC | GCT | ACT | AAA | TGC | AGA | CTG | GAG | GGG | ACC | AAA | 1548 |
| Ser 525 | Ser | Cys | His | Leu | Phe 530 | Ala | Thr | Lys | Cys | Arg 535 | Leu | Glu | Gly | Thr | Lys 540 | |
| AAG | GGG | CAT | CAA | CTC | CAG | CTG | GAT | TAT | TTT | GGA | GCC | TGC | AAA | TCT | ATT | 1596 |
| Lys | Gly | His | Gln | Leu 545 | Gln | Leu | Asp | Tyr | Phe 550 | Gly | Ala | Cys | Lys | Ser 555 | Ile | |
| CCT | ACT | TGT | ACG | GAC | TTT | GAA | GTG | ATT | CAG | TTT | CCT | CTA | CGG | ATG | AGA | 1644 |
| Pro | Thr | Cys | Thr | Asp 560 | Phe | Glu | Val | Ile | Gln 565 | Phe | Pro | Leu | Arg | Met 570 | Arg | |
| GAC | TGG | CTC | AAG | AAT | ATC | CTC | ATG | CAG | CTT | TAT | GAA | GCC | AAC | TCT | GAA | 1692 |
| Asp | Trp | Leu 575 | Lys | Asn | Ile | Leu | Met 580 | Gln | Leu | Tyr | Glu | Ala 585 | Asn | Ser | Glu | |
| CAC | GCT | GGT | TAT | CTA | AAT | GAG | AAG | CAG | AGA | AAT | AAA | GTC | AAG | AAA | ATT | 1740 |
| His | Ala | Gly | Tyr 590 | Leu | Asn | Glu | Lys | Gln 595 | Arg | Asn | Lys | Val | Lys 600 | Lys | Ile | |
| TAC | CTG | GAT | GAA | AAG | AGG | CTT | TTG | GCT | GGG | GAC | CAT | CCC | ATT | GAC | CTT | 1788 |
| Tyr 605 | Leu | Asp | Glu | Lys | Arg 610 | Leu | Leu | Ala | Gly | Asp 615 | His | Pro | Ile | Asp | Leu 620 | |
| CTC | TTA | AGG | GAC | TTT | AAG | AAA | AAC | TAC | CAC | ATG | TAT | GTG | TAT | CCT | GTG | 1836 |
| Leu | Leu | Arg | Asp | Phe 625 | Lys | Lys | Asn | Tyr | His 630 | Met | Tyr | Val | Tyr | Pro 635 | Val | |
| CAC | TGG | CAG | TTT | AGT | GAA | CTT | GAC | CAA | CAC | CCT | ATG | GAT | AGA | GTC | TTG | 1884 |
| His | Trp | Gln | Phe 640 | Ser | Glu | Leu | Asp | Gln 645 | His | Pro | Met | Asp | Arg 650 | Val | Leu | |

-continued

| | | | | | | | | | | | | | | | | |
|---|---|---|---|---|---|---|---|---|---|---|---|---|---|---|---|---|
| ACA | CAT | TCT | GAA | CTT | GCT | CCT | CTG | CGA | GCA | TCT | CTG | GTG | CCC | ATG | GAA | 1932 |
| Thr | His | Ser | Glu | Leu | Ala | Pro | Leu | Arg | Ala | Ser | Leu | Val | Pro | Met | Glu | |
| | | 655 | | | | 660 | | | | | | 665 | | | | |
| CAC | TGC | ATA | ACC | CGT | TTC | TTT | GAG | GAG | TGT | GAC | CCC | AAC | AAG | GAT | AAG | 1980 |
| His | Cys | Ile | Thr | Arg | Phe | Phe | Glu | Glu | Cys | Asp | Pro | Asn | Lys | Asp | Lys | |
| | 670 | | | | | 675 | | | | | 680 | | | | | |
| CAC | ATC | ACC | CTG | AAG | GAG | TGG | GGC | CAC | TGC | TTT | GGA | ATT | AAA | GAA | GAG | 2028 |
| His | Ile | Thr | Leu | Lys | Glu | Trp | Gly | His | Cys | Phe | Gly | Ile | Lys | Glu | Glu | |
| 685 | | | | | 690 | | | | 695 | | | | | | 700 | |
| GAC | ATA | GAT | GAA | AAT | CTC | TTG | TTT | TG | AACGAAGATT | | TTAAAGAACT | | | | | 2074 |
| Asp | Ile | Asp | Glu | Asn | Leu | Leu | Phe | | | | | | | | | |
| | | | | 705 | | | | | | | | | | | | |

CAACTTTCCA GCATCCTCCT CTGTTCTAAC CACTTCAGAA ATATATGCAG CTGTGATACT 2134

TGTAGATTTA TATTTAGCAA AATGTTAGCA TGTATGACAA GACAATGAGA GTAATTGCTT 2194

GACAACAACC TATGCACCAG GTATTAACA TTAACTTTGG AAACAAAAAT GTACAATTAA 2254

GTAAAGTCAA CATATGCAAA ATACTGTACA TTGTGAACAG AAGTTTAATT CATAGTAATT 2314

TCACTCTCTG CATTGACTTA TGAGATAATT AATGATTAAA CTATTAATGA TAAAAATAAT 2374

GCATTTGTAT TGTTCATAAT ATCATGTGCA CTTCAAGAAA ATGGAATGCT ACTCTTTTGT 2434

GGTTTACGTG TATTATTTTC AATATCTTAA T 2465

( 2 ) INFORMATION FOR SEQ ID NO:6:

( i ) SEQUENCE CHARACTERISTICS:
        ( A ) LENGTH: 664 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:6:

| | | | | | | | | | | | | | | |
|---|---|---|---|---|---|---|---|---|---|---|---|---|---|---|
| Met | Lys | Thr | Gly | Leu | Phe | Phe | Leu | Cys | Leu | Leu | Gly | Thr | Ala | Ala | Ala |
| 1 | | | | 5 | | | | | 10 | | | | | 15 | |
| Ile | Pro | Thr | Asn | Ala | Arg | Leu | Leu | Ser | Asp | His | Ser | Lys | Pro | Thr | Ala |
| | | | 20 | | | | | 25 | | | | | 30 | | |
| Glu | Thr | Val | Ala | Pro | Asp | Asn | Thr | Ala | Ile | Pro | Ser | Leu | Arg | Ala | Glu |
| | | 35 | | | | | 40 | | | | | 45 | | | |
| Asp | Glu | Glu | Asn | Glu | Lys | Glu | Thr | Ala | Val | Ser | Thr | Glu | Asp | Asp | Ser |
| | 50 | | | | | 55 | | | | | 60 | | | | |
| His | His | Lys | Ala | Glu | Lys | Ser | Ser | Val | Leu | Lys | Ser | Lys | Glu | Glu | Ser |
| 65 | | | | | 70 | | | | | 75 | | | | | 80 |
| His | Glu | Gln | Ser | Ala | Glu | Gln | Gly | Lys | Ser | Ser | Ser | Gln | Glu | Leu | Gly |
| | | | | 85 | | | | | 90 | | | | | 95 | |
| Leu | Lys | Asp | Gln | Glu | Asp | Ser | Asp | Gly | Asp | Leu | Ser | Val | Asn | Leu | Glu |
| | | | | 100 | | | | | 105 | | | | | 110 | |
| Tyr | Ala | Pro | Thr | Glu | Gly | Thr | Leu | Asp | Ile | Lys | Glu | Asp | Met | Ser | Glu |
| | | | 115 | | | | | 120 | | | | | 125 | | |
| Pro | Gln | Glu | Lys | Lys | Leu | Ser | Glu | Asn | Thr | Asp | Phe | Leu | Ala | Pro | Gly |
| | | 130 | | | | | 135 | | | | | 140 | | | |
| Val | Ser | Ser | Phe | Thr | Asp | Ser | Asn | Gln | Glu | Ser | Ile | Thr | Lys | Arg | |
| 145 | | | | | 150 | | | | | 155 | | | | | 160 |
| Glu | Glu | Asn | Gln | Glu | Gln | Pro | Arg | Asn | Tyr | Ser | His | His | Gln | Leu | Asn |
| | | | | 165 | | | | | 170 | | | | | 175 | |
| Arg | Ser | Ser | Lys | His | Ser | Gln | Gly | Leu | Arg | Asp | Gln | Gly | Asn | Gln | Glu |
| | | | 180 | | | | | 185 | | | | | 190 | | |
| Gln | Asp | Pro | Asn | Ile | Ser | Asn | Gly | Glu | Glu | Glu | Glu | Glu | Lys | Glu | Pro |
| | | | 195 | | | | | 200 | | | | | 205 | | |

-continued

| | | | | | | | | | | | | | |
|---|---|---|---|---|---|---|---|---|---|---|---|---|---|
| Gly | Glu | Val | Gly | Thr | His | Asn | Asp | Asn | Gln | Glu | Arg | Lys | Thr | Glu | Leu |
| | 210 | | | | 215 | | | | 220 | | | | |
| Pro | Arg | Glu | His | Ala | Asn | Ser | Lys | Gln | Glu | Asp | Asn | Thr | Gln | Ser |
| 225 | | | | 230 | | | | 235 | | | | 240 |
| Asp | Asp | Ile | Leu | Glu | Glu | Ser | Asp | Gln | Pro | Thr | Gln | Val | Ser | Lys | Met |
| | | | | 245 | | | | 250 | | | | 255 |
| Gln | Glu | Asp | Glu | Phe | Asp | Gln | Gly | Asn | Gln | Glu | Gln | Glu | Asp | Asn | Ser |
| | | | 260 | | | | 265 | | | | 270 |
| Asn | Ala | Glu | Met | Glu | Glu | Glu | Asn | Ala | Ser | Asn | Val | Asn | Lys | His | Ile |
| | | 275 | | | | 280 | | | | 285 |
| Gln | Glu | Thr | Glu | Trp | Gln | Ser | Gln | Glu | Gly | Lys | Thr | Gly | Leu | Glu | Ala |
| | 290 | | | | 295 | | | | 300 |
| Ile | Ser | Asn | His | Lys | Glu | Thr | Glu | Glu | Lys | Thr | Val | Ser | Glu | Ala | Leu |
| 305 | | | | 310 | | | | 315 | | | | 320 |
| Leu | Met | Glu | Pro | Thr | Asp | Asp | Gly | Asn | Thr | Thr | Pro | Arg | Asn | His | Gly |
| | | | 325 | | | | 330 | | | | 335 |
| Val | Asp | Asp | Asp | Gly | Asp | Asp | Asp | Gly | Asp | Gly | Gly | Thr | Asp | Gly |
| | | | 340 | | | | 345 | | | | 350 |
| Pro | Arg | His | Ser | Ala | Ser | Asp | His | Tyr | Phe | Ile | Pro | Ser | Gln | Ala | Phe |
| | | 355 | | | | 360 | | | | 365 |
| Leu | Glu | Ala | Glu | Arg | Ala | Gln | Ser | Ile | Ala | Tyr | His | Leu | Lys | Ile | Glu |
| | 370 | | | | 375 | | | | 380 |
| Glu | Gln | Arg | Glu | Lys | Val | His | Glu | Asn | Glu | Asn | Ile | Gly | Thr | Thr | Glu |
| 385 | | | | 390 | | | | 395 | | | | 400 |
| Pro | Gly | Glu | His | Gln | Glu | Ala | Lys | Lys | Ala | Glu | Asn | Ser | Ser | Asn | Glu |
| | | | 405 | | | | 410 | | | | 415 |
| Glu | Glu | Thr | Ser | Ser | Glu | Gly | Asn | Met | Arg | Val | His | Ala | Val | Asp | Ser |
| | | | 420 | | | | 425 | | | | 430 |
| Cys | Met | Ser | Phe | Gln | Cys | Lys | Arg | Gly | His | Ile | Cys | Lys | Ala | Asp | Gln |
| | | 435 | | | | 440 | | | | 445 |
| Gln | Gly | Lys | Pro | His | Cys | Val | Cys | Gln | Asp | Pro | Val | Thr | Cys | Pro | Pro |
| | 450 | | | | 455 | | | | 460 |
| Thr | Lys | Pro | Leu | Asp | Gln | Val | Cys | Gly | Thr | Asp | Asn | Gln | Thr | Tyr | Ala |
| 465 | | | | 470 | | | | 475 | | | | 480 |
| Ser | Ser | Cys | His | Leu | Phe | Ala | Thr | Lys | Cys | Arg | Leu | Glu | Gly | Thr | Lys |
| | | | 485 | | | | 490 | | | | 495 |
| Lys | Gly | His | Gln | Leu | Gln | Leu | Asp | Tyr | Phe | Gly | Ala | Cys | Lys | Ser | Ile |
| | | | 500 | | | | 505 | | | | 510 |
| Pro | Thr | Cys | Thr | Asp | Phe | Glu | Val | Ile | Gln | Phe | Pro | Leu | Arg | Met | Arg |
| | | 515 | | | | 520 | | | | 525 |
| Asp | Trp | Leu | Lys | Asn | Ile | Leu | Met | Gln | Leu | Tyr | Glu | Ala | Asn | Ser | Glu |
| | 530 | | | | 535 | | | | 540 |
| His | Ala | Gly | Tyr | Leu | Asn | Glu | Lys | Gln | Arg | Asn | Lys | Val | Lys | Lys | Ile |
| 545 | | | | 550 | | | | 555 | | | | 560 |
| Tyr | Leu | Asp | Glu | Lys | Arg | Leu | Leu | Ala | Gly | Asp | His | Pro | Ile | Asp | Leu |
| | | | 565 | | | | 570 | | | | 575 |
| Leu | Leu | Arg | Asp | Phe | Lys | Lys | Asn | Tyr | His | Met | Tyr | Val | Tyr | Pro | Val |
| | | | 580 | | | | 585 | | | | 590 |
| His | Trp | Gln | Phe | Ser | Glu | Leu | Asp | Gln | His | Pro | Met | Asp | Arg | Val | Leu |
| | | 595 | | | | 600 | | | | 605 |
| Thr | His | Ser | Glu | Leu | Ala | Pro | Leu | Arg | Ala | Ser | Leu | Val | Pro | Met | Glu |
| | 610 | | | | 615 | | | | 620 |
| His | Cys | Ile | Thr | Arg | Phe | Phe | Glu | Glu | Cys | Asp | Pro | Asn | Lys | Asp | Lys |

-continued

```
            625                     630                    635                        640
His  Ile  Thr  Leu  Lys  Glu  Trp  Gly  His  Cys  Phe  Gly  Ile  Lys  Glu  Glu
                     645                      650                    655
Asp  Ile  Asp  Glu  Asn  Leu  Leu  Phe
                660
```

HP-8 AUTOANTIGEN

This application is a continuation-in-part application of U.S. Ser. No. 08/316,068, filed Sep. 30, 1994, now abaondened, which is in turn a continuation application of U.S. Ser. No. 08/033,120, filed Mar. 18, 1993, now abandoned, the entire contents of each of which are hereby incorporated by reference herein.

BACKGROUND OF THE INVENTION

1. Field of the Invention

The present invention relates generally to connective tissue diseases such as rheumatoid arthritis and systemic lupus erythematosus (SLE). More particularly, the present invention relates to antigens which are related to such diseases.

2. Description of Related Art

Systemic lupus erythematosus (SLE) is a chronic inflammatory disease which results in injury to the skin, joints, kidneys, nervous system and mucous membranes. SLE is not limited to these areas and can affect any organ of the body. SLE is an extremely debilitating diseases which is present in approximately one person in 800. The high frequency of SLE and its debilitating nature have resulted in intense study of this disease by the medical community.

In spite of the intense investigation the etiology of SLE is for the most part unknown. SLE is an autoimmune connective tissue disease which is characterized by the presence of a high level of autoantibodies. Patients with SLE typically have a wide variety of autoantibodies against nuclear and cytoplasmic cellular components. The antinuclear antibodies are known to be directed against a variety of materials including deoxyribonucleoprotein, DNA and histone. An exemplary antibody which has been associated with SLE is the 3E10 anti-DNA antibody (see Weisbart, et al., A CONSERVED ANTI-DNA ANTIBODY IDIOTYPE ASSOCIATED WITH NEPHRITIS IN MURINE AND HUMAN SYSTEMIC LUPUS ERYTHEMATOSUS, Journal of Immunology, Vol. 144, 2653–2658, No. 7, April 1990; U.S. Pat. No. 4,812,397).

The cause of SLE has not been established. However, factors that appear to contribute to the development of SLE include exposure to sunlight, genetic predisposition to the disease, certain drugs, viral and bacterial infection and hormonal influences. To complicate matters further, the clinical manifestations of SLE are confusingly diverse. There is no specific cure for SLE since the underlying pathologies are not known. Accordingly, treatment involves supportive measures employed to prevent or minimize acute relapses and provide relief from symptoms.

In view of the above, there is a continuing need to investigate the etiology of SLE and other inflammatory diseases in order to develop effective procedures for prevention and treatment.

As part of this investigation, it is important that the various antigens, antibodies and other factors involved in SLE be isolated and identified so that their role in SLE can be established.

SUMMARY OF THE INVENTION

In accordance with the present invention, an antigen has been identified and isolated which is related to SLE. The antigen has been identified as HP-8. The HP-8 antigen is expressed by a gene which was identified by immunoscreening a human placental cDNA gt11 expression library with the 3E10 antibody mentioned above. The isolated cDNA gene sequence (insert size 132 bp) was found to hybridize to a 3.3 kb and 1.2 kb mRNA transcript. It was found that the 3.3 kb transcript was expressed in brain, heart, placenta, lung, skeletal muscle and pancreatic tissues. The 1.2 kb transcript was found to be present in brain, heart, lung, skeletal muscle and kidney.

As a feature of the present invention, proteins which include the HP-8 antigen epitope are produced by recombinant means involving culturing of transformed microorganisms which include the gene which codes on expression for the HP-8 antigen.

The HP-8 antigen is useful in mapping and determining the genetic origin for expression of gene products in patients with SLE. In addition, the HP-8 antigen may be used in procedures for developing therapeutic rational drug designs to be used in treating SLE or other related connective tissue diseases such as rheumatoid arthritis.

As another feature of the present invention, proteins and polypeptides which include the HP-8 antigen are used to raise antibodies in animals. The antibodies which are raised in response to the HP-8 antigen are useful in the study and treatment of SLE.

The above-described and many other features and attendant advantages of the present invention will become better understood by reference to the following detailed description when taken in conjunction with the accompanying drawings.

BRIEF DESCRIPTION OF THE DRAWINGS

FIGS. 2A-1 through 2A-8 shows the nucleotide and corresponding amino acid sequence of the full length HP-8 clone.

DETAILED DESCRIPTION OF THE INVENTION

The HP-8 antigen in accordance with the present invention is defined as a protein or polypeptide which includes an epitope which is substantially homologous with the amino acid sequence set forth in SEQ ID NO. 4. The protein or polypeptide will have a molecular weight of less than 100 KD. Preferred proteins will have molecular weights on the order of 60 to 100 Kd. To be considered substantially homologous, the amino acid sequence of the epitope of the protein or polypeptide must be at least about 90% or more homologous with the amino acid sequence set forth in SEQ ID NO. 4. Proteins and polypeptides which fall under the definition of HP-8 must bind 3E10 antibody. Such HP-8 proteins and polypeptides are also expected to bind calcium, hydroxyapatite and collagen.

Preferably, the HP-8 antigen has the amino acid sequence set forth in SEQ ID No. 6 or its amino acid sequence variants. Most preferably, the HP-8 antigen has the amino acid sequence set forth in SEQ ID No. 6. Amino acid sequence variants of the HP-8 antigen having the amino acid sequence set forth in SEQ ID No. 6 fall into one or more of three classes: substitutional, insertional and deletional variants. These variants ordinarily are prepared by site specific mutagenesis of nucleotides in the DNA encoding the variant, and thereafter expressing the DNA in recombinant cell culture. However, variants having up to about 100–150 residues may be conveniently prepared using in vitro synthesis.

Amino acid substitutions are typically of single residues; insertions will be on the order of about from 1 to 10 amino acids; and deletions will range from about 1 to 30 amino acids. Deletions and insertions preferably are made in adjacent pairs, i.e. a deletion of 2 residues or insertion of 2 residues. Substitutions, deletions, insertions or any combination thereof may be combined to arrive at a final construct. Obviously, the mutations made in the DNA encoding the variant HP-8 antigen must not place the sequence out of reading frame.

Insertional amino acid sequence variants of the HP-8 antigen are those in which one or more amino acid residues are introduced into a predetermined site. Most commonly, insertional variants are fusions of heterologous proteins or polypeptides to the amino or carboxyl terminus of the HP-8 antigen.

Amino acid sequence variants of the HP-8 antigen having the amino acid sequence set forth in SEQ ID No. 6 must, as stated above, have an epitope which is substantially homologous (i.e. 90% homologous) with the amino acid sequence set forth in SEQ ID No. 4. Further, the entire protein or polypeptide will have a molecular weight of less than 100 Kd, preferably between about 60 and 100 Kd. In addition, the amino acid sequence variants of HP-8 having the amino acid sequence set forth in SEQ ID No. 6 must potentially bind 3E10 antibody, i.e. must be capable of binding the antibody to substantially the same extent as HP-8 antigen having an epitope having the sequence set forth in SEQ ID No. 4.

HP-8 antigens in accordance with the present invention may be produced in accordance with any of the known processes for preparing polypeptides and proteins. It is preferred that the antigen be expressed in prokaryotic, eukaryotic or insect viral cells by recombinant means. An exemplary procedure for producing HP-8 antigen is as follows:

A commercially available cDNA library was plated and screened according to manufacturers instructions. The cDNA library was a human placental cDNA GT11 expression library, Catalog No: HL-1075B (Clontech Laboratories, Palo Alto, Calif.). Large 150 mm LB agar plates were used to plate and screen the library with MAb 3E10. 0.6 ml of plating bacteria (Y1090) was incubated with a proper dilution of lambda gt11 phage and absorbed to the cells at 370° C. for 15 minutes. 7.5 ml of LB soft agarose was added to the culture and quickly poured onto the plates and incubated at 42° C. for 3.5 hours. Plates were removed and overlaid with a dry nitrocellulose filter previously saturated in 10 mM Isopropyl-1-thio-B-D-galactoside (IPTG). The plates were incubated for an additional 3.5 hours at 37° C. Filters were removed and rinsed in 50 mM tris (pH 7.9), 150 mM NaCl, 0.05% TWEEN (TBST) buffers. Filters were incubated with 10 ug/ml of MAb in TBST buffer for 3 hours at room temperature. Following incubation filters were washed in three changes of Buffer A for 3 minutes each. Detection of bound antibody was done using the CLIK II Immunoscreening Kit (Clontech Laboratories, Palo Alto, Calif., Catalog number: K1004-2).

Detection of bound antibody used an alkaline phosphatase conjugate. Filters were incubated with goat-anti-mouse conjugate (2 ul) in 5 ml of buffer A for 30 minutes. Following incubation the filters were washed 3 times with 50 ml of Buffer A (10 minutes each wash). An additional wash was done in Buffer C for 10 minutes. Detection was performed by addition of 25 ul NBT (100 mg/ml) and 12 ul 5-Bromo-4-chloro-3-indolyl phosphate (BCIP) (100 mg/ml). Filters were incubated until signals became visible under reduced illumination. The reaction was terminated by washing in 1 mM EDTA and positives selected. Six positives were identified in the screen and one was determined to be a true positive following secondary and tertiary rescreening using dilution cloning. The positive, designated HP-8, was screened against normal human sera as a negative control indicating the validity of the 3E10 reactivity. Details of the preparation of the buffers are described in the Clontech Handbook (1992).

The lambda phage was grown up on plates according to protocols supplied from Clontech (pgs. 20–22, Clontech Protocol Handbook 1992). Isolated DNA was obtained and Eco R1 digested using standard methods described in Maniatis, T. et al., (1989) Molecular Cloning: A Laboratory Manual. 2nd Ed. (Cold Spring Harbor Laboratory Press; Plainview, N.Y.). An insert of approximately 200 bases was resolved when electrophoresed in a 1% agarose gel in TBE. The insert was PCR amplified according to manufacturers instructions and subcloned into pCR II. (Invitrogen, San Diego, Calif., Catalog K2000-01). The subcloned fragment was retained as a hard copy template for subsequent expression cloning. Additional PCR amplification of insert was performed to generate material for subcloning into pBLUE-SCRIPT for DNA sequencing. (Stratagene, La Jolla, Calif., Catalog number: 212205).

The double-stranded pBLUESCRIPT pSKII+ plasmids containing the HP-8 specific clone fragment were grown and DNA harvested using the Qiagen column purification system (Qiagen Corp., Chatsworth, Calif., Catalog number: 12162). T3 and T7 primers were used to sequence the cDNA. Procedures were followed using standard cycle sequencing conditions recommended by the manufacturers (ABI, Foster City, Calif., Catalog number: 401384). The nucleotide sequence and corresponding amino acid sequence are set forth in SEQ ID NO: 1 and SEQ ID NO: 2, respectively.

The nucleotide sequence set forth in SEQ ID No. 1 has a length of 154 bp. The corresponding amino acid sequence (SEQ ID Nos. 1 & 2) is 51 amino acids in length. However, as is well known, cDNA clones from libraries often contain artifactual DNA sequence inserts at the termini of the sequence actually corresponding to mRNA. In accordance with this, it was determined that the actual size of the HP-8 insert was 132 bp and the corresponding amino acid sequence was 44 amino acids (SEQ ID Nos. 3 & 4).

Figure 1:
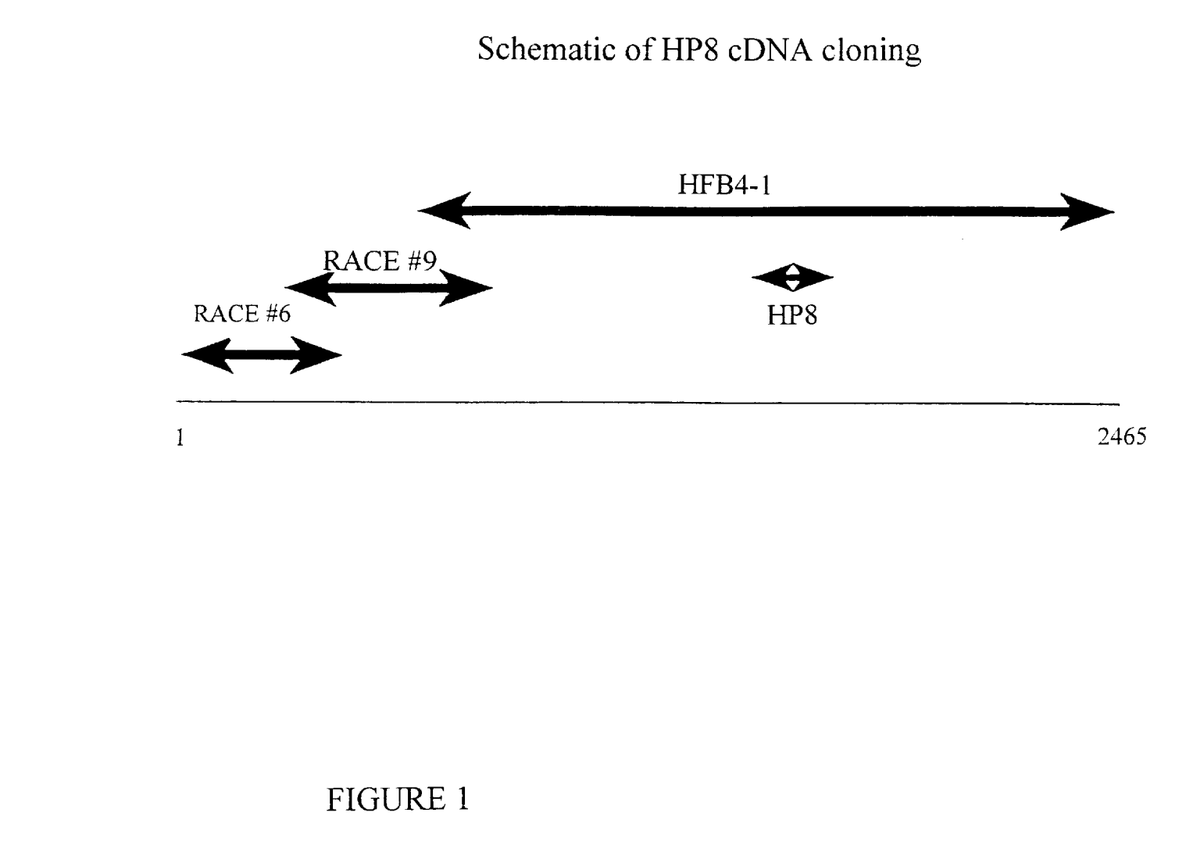
FIG. 1 shows a schematic of HP-8 cDNA cloning.
Figure 2A:
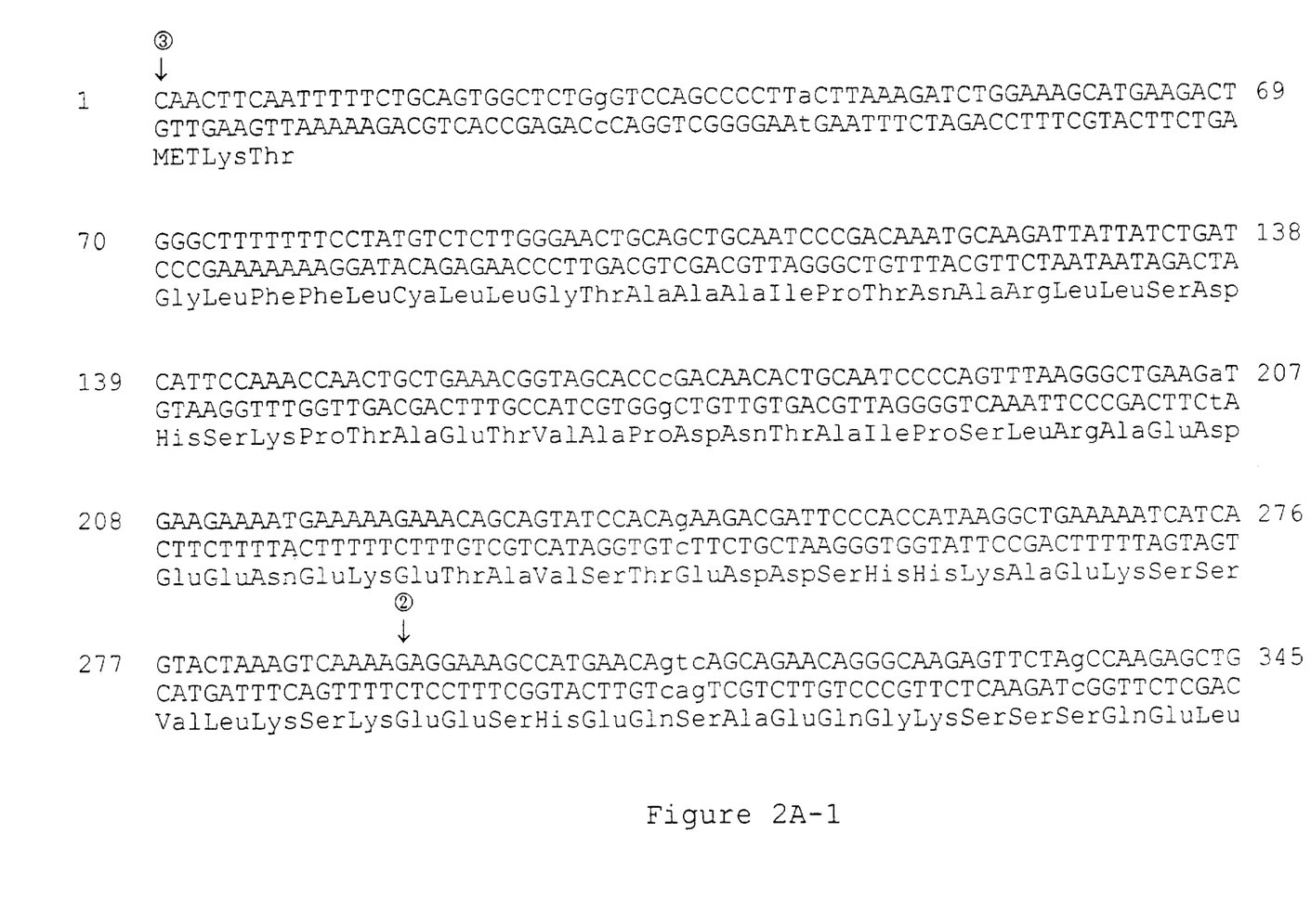
Figure 2A:
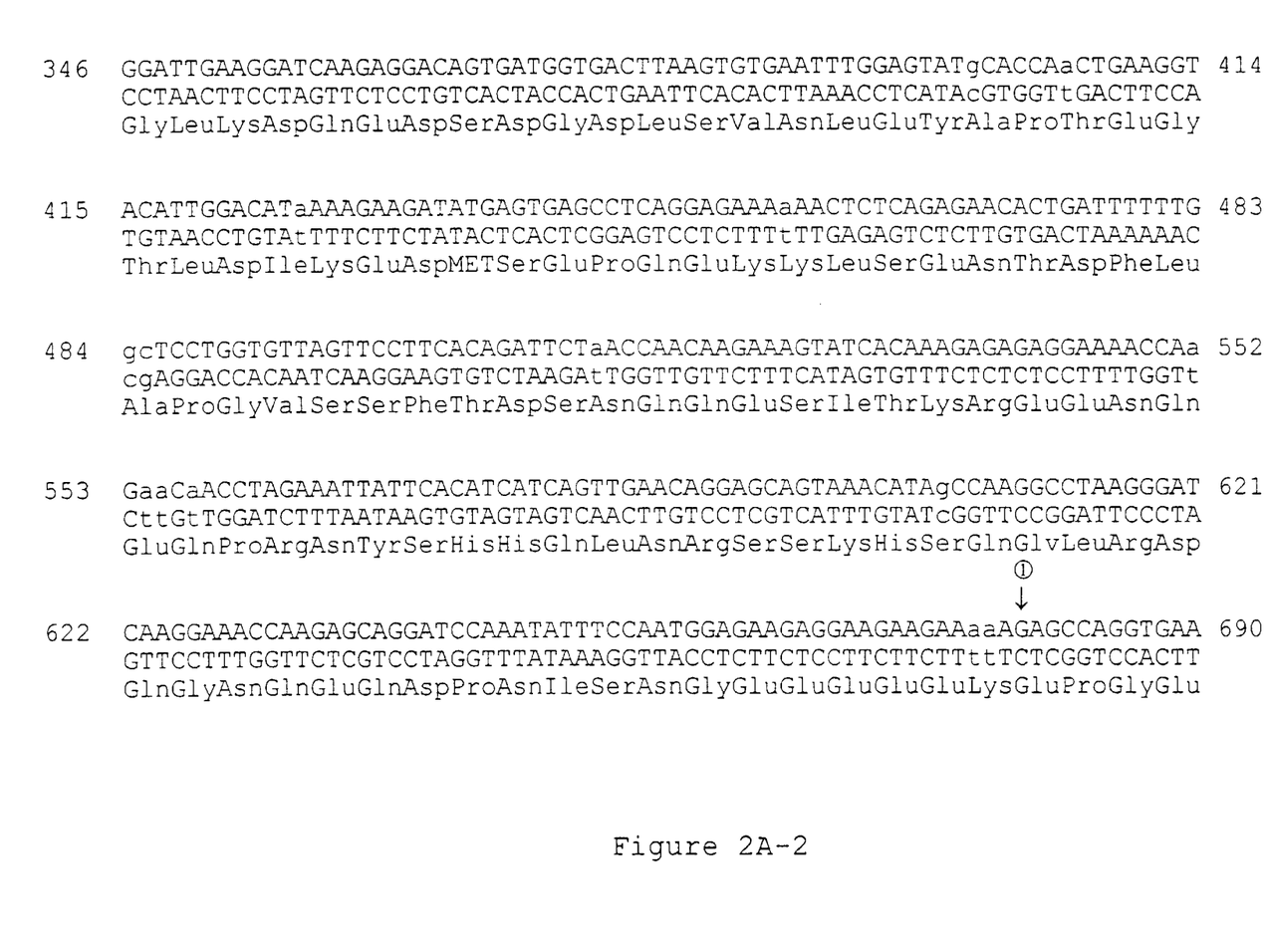
Figure 2A:
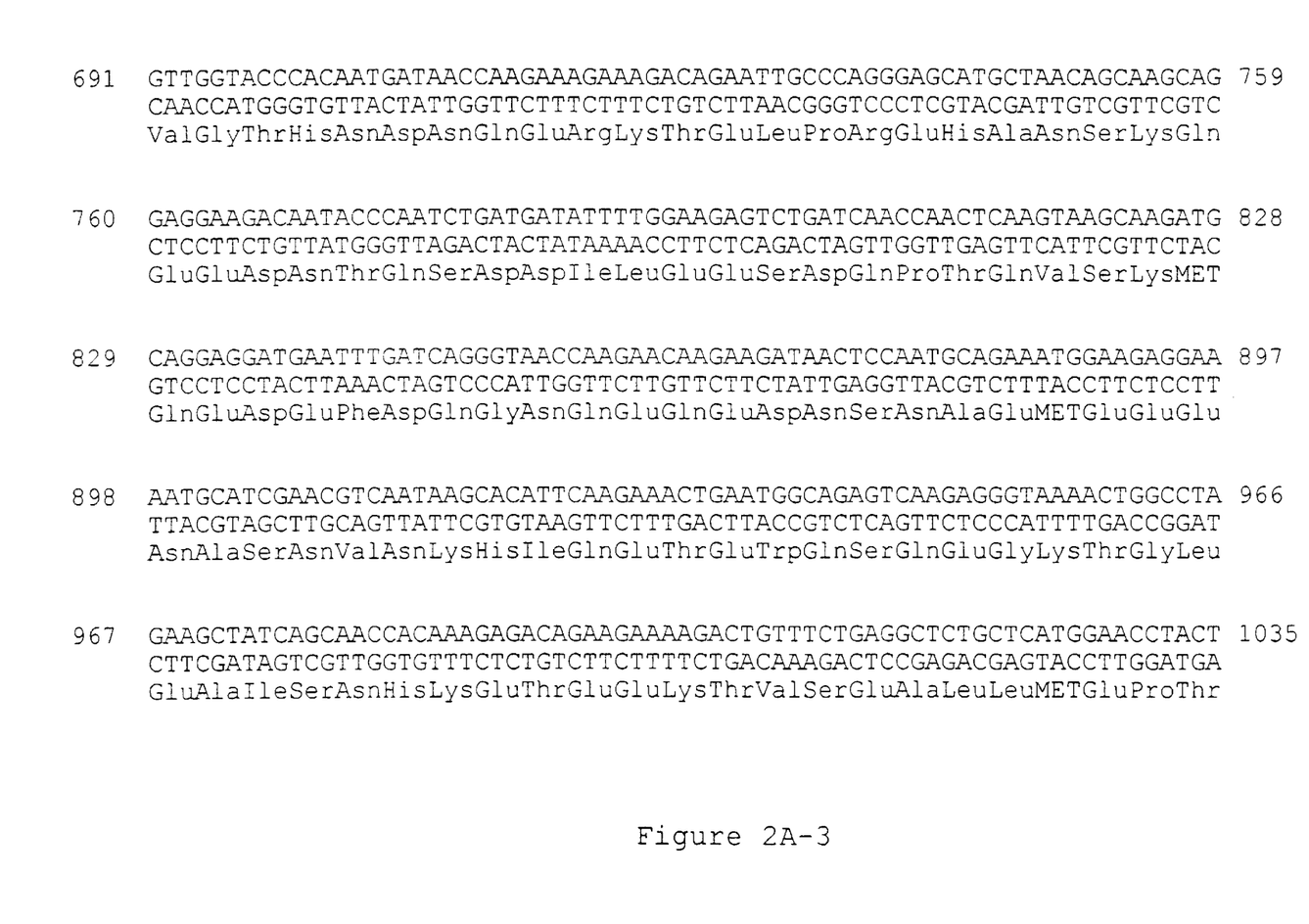
Figure 2A:
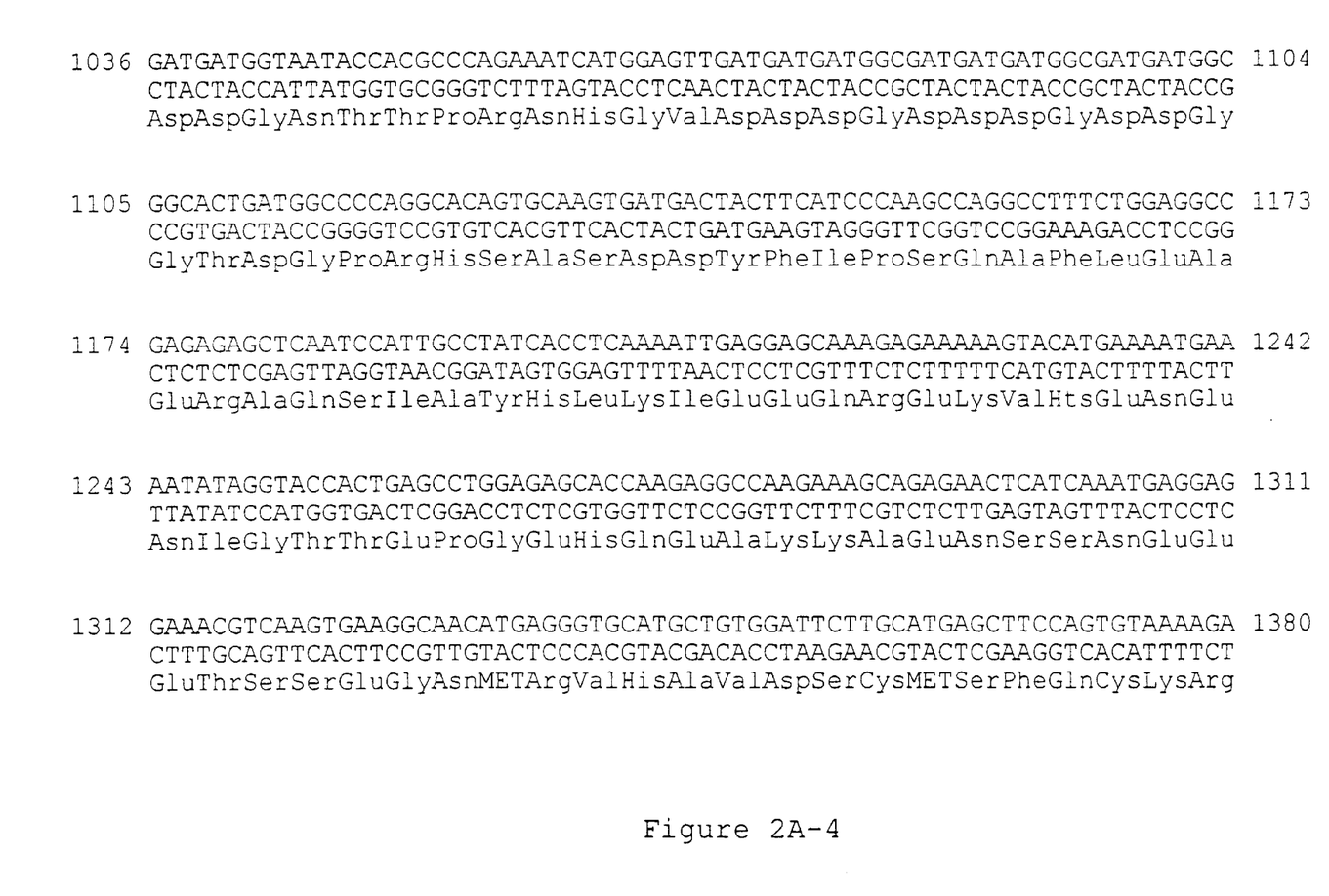
Figure 2A:
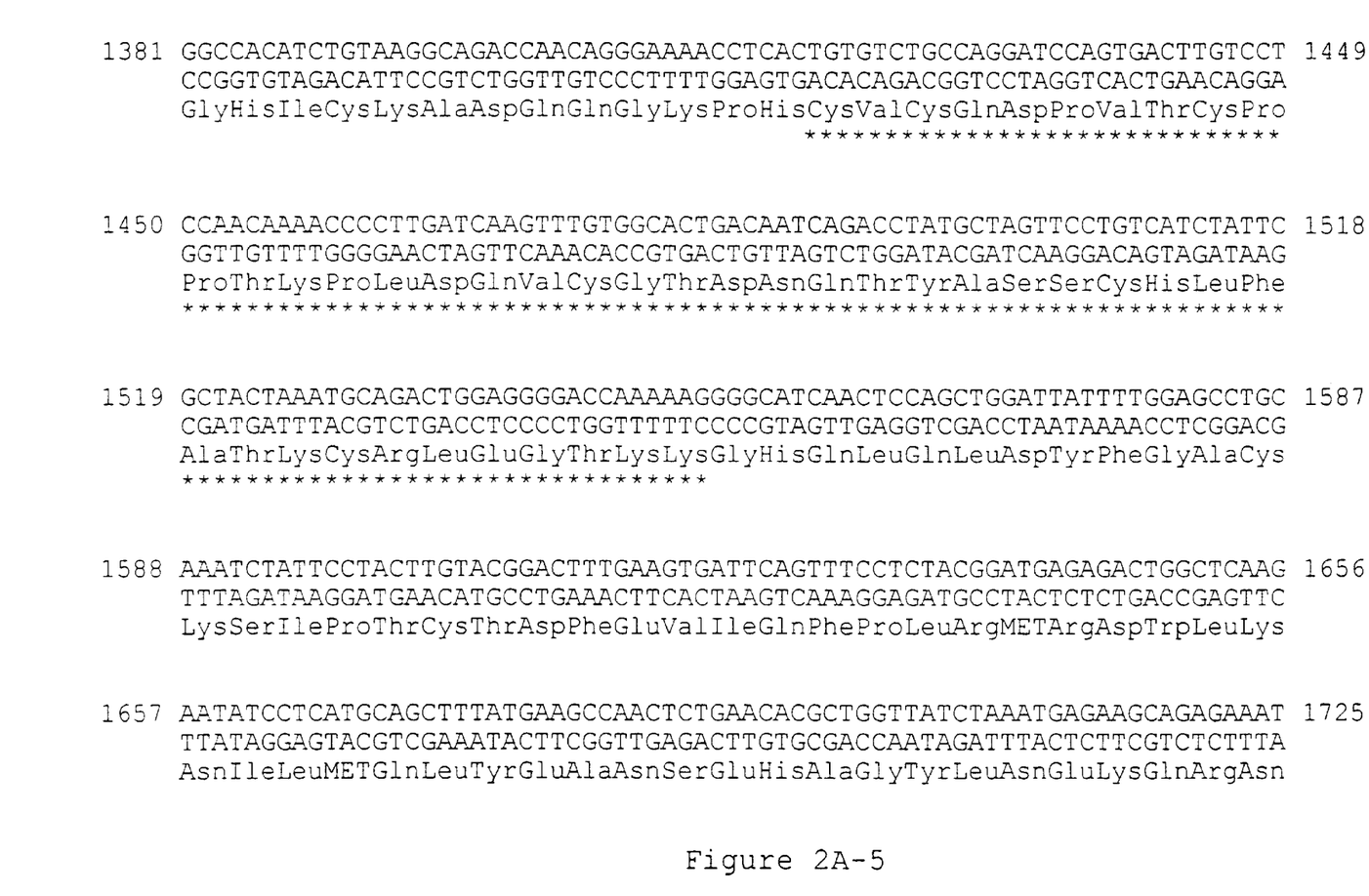
Figure 2A:
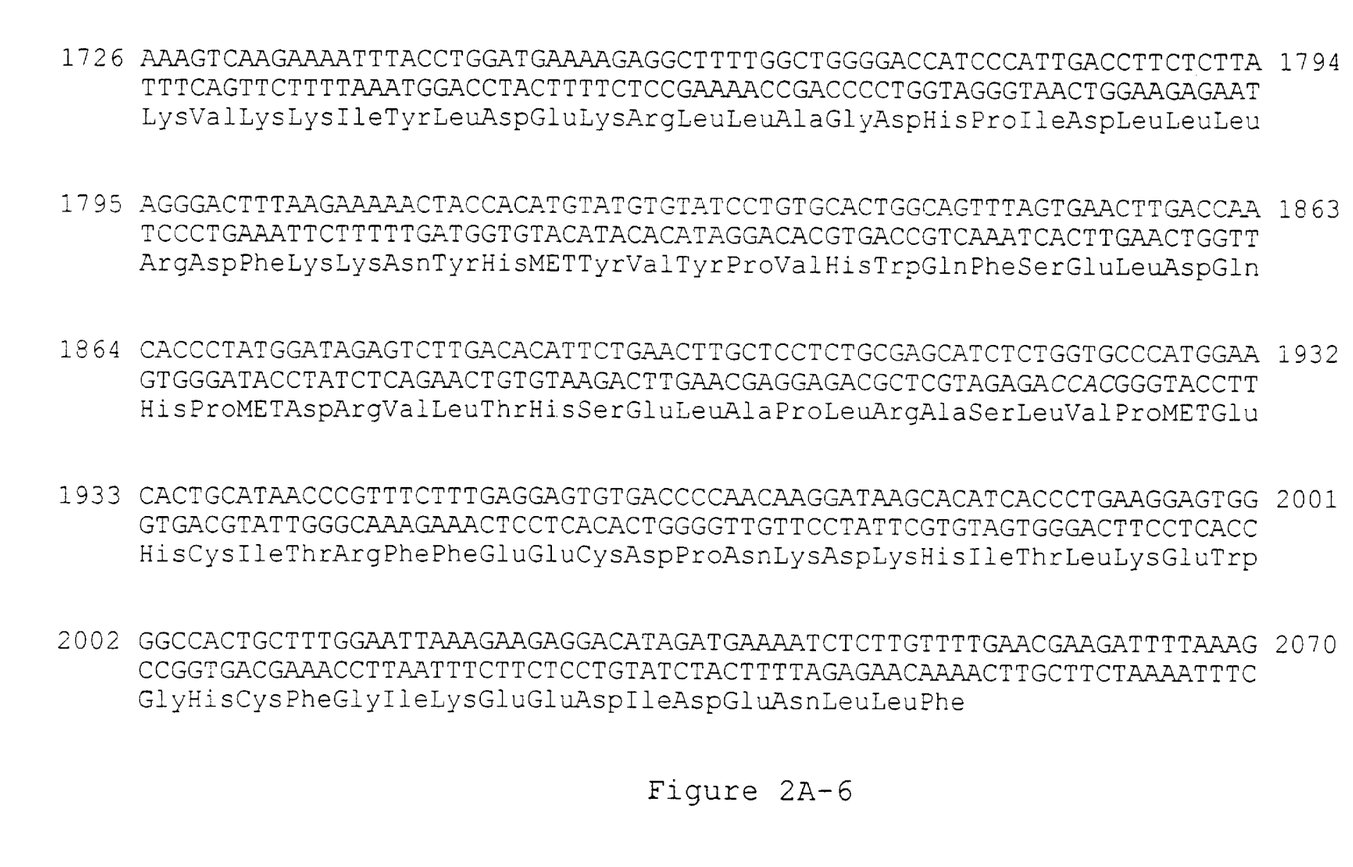
Figure 2A:
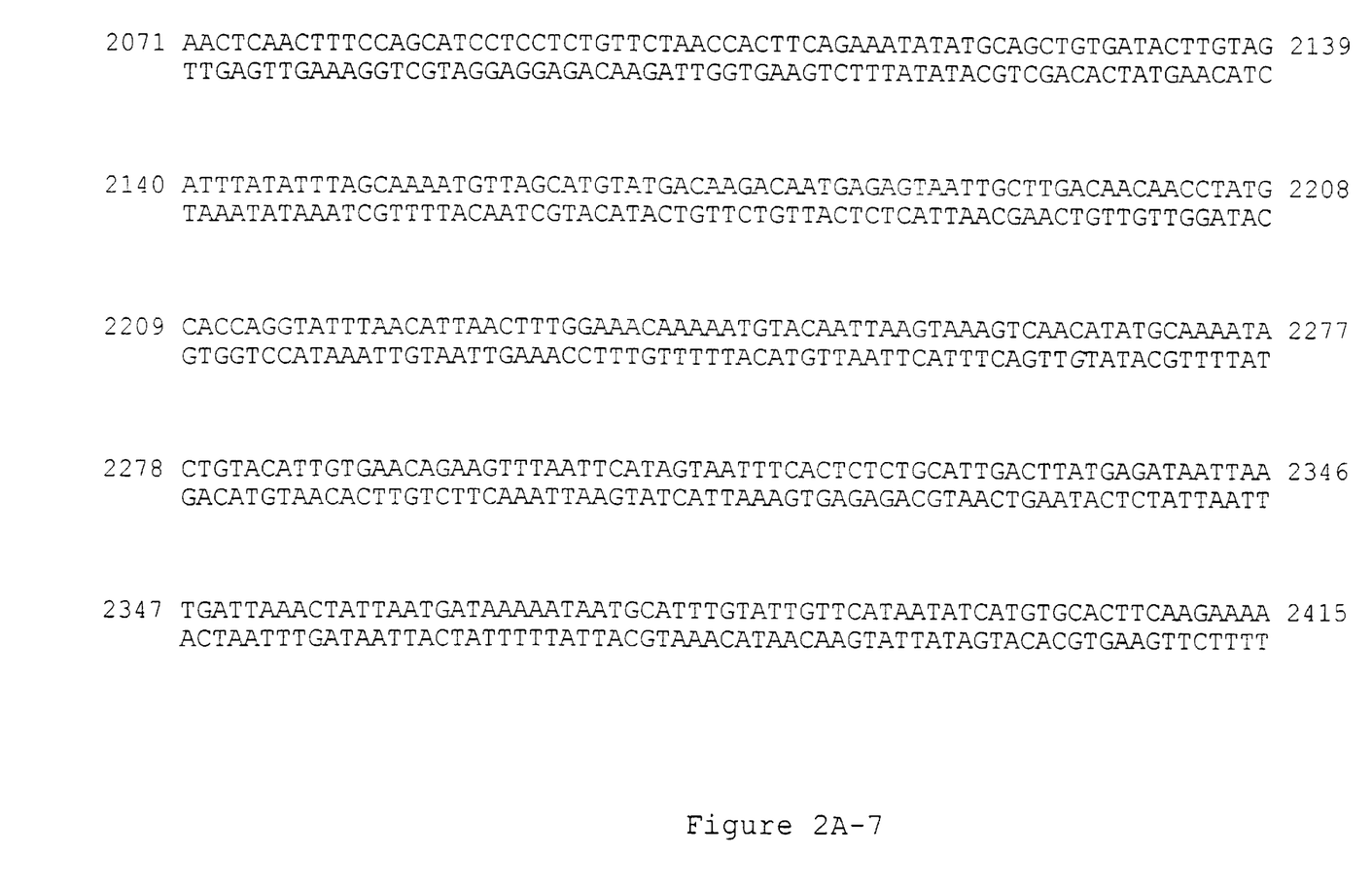
Figure 2A:
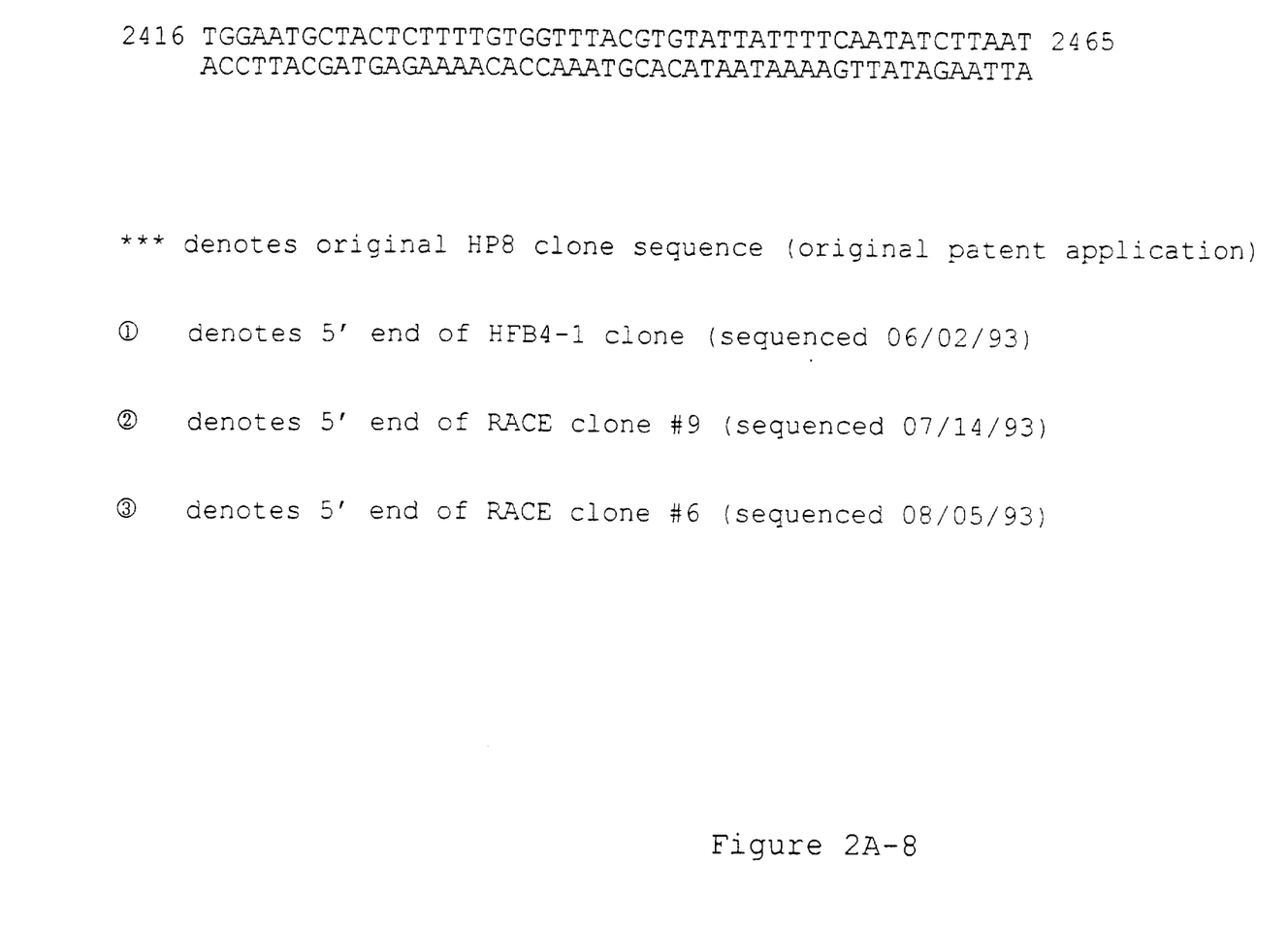

In order to obtain full length coding sequences for HP8, a human fetal brain cDNA expression library in Lambda Zap II (Stratagene, Cat. #936206) was screened by DNA hybridization to the 132 bp HP8 cDNA insert isolated from the immunoscreen. Brain was chosen as tissue source because Northern hybridization results indicated that HP-8 was highly expressed in this tissue. Hybridizing clones were purified and rescued to pBluescript SKII+ (Stratagene) plasmids containing HP8 hybridizing cDNA inserts. Clones were first sequenced from the ends using T3 and T7 promoter primers and with HP-8 specific primers to verify authenticity as an overlapping HP-8 cDNA sequence. The sequence of the largest overlapping clone, HFB4-1 (1790 bp) was determined in its entirety along both strands by using nested primers, assembled using GEL software (Intelligenetics), and is included in FIG. 1. Translation of the nucleotide sequence in all reading frames revealed a single ORF encoding a 459 amino acid sequence. HFB4-1 appears to be a truncated cDNA clone (deficient in 5' sequences), that encodes the C-terminal 459 amino acids of HP-8, and approximately 400 bp of 3' untranslated (UT) nucleotide sequence. A putative poly-A addition site is just upstream from the 3' end of the clone, indicating that HFB4-1 contains the authentic 3' end of the mRNA.

Southern blot analyses, using genomic DNA (human, monkey, rat, mouse, dog, cow, rabbit, chicken, and yeast) (Clontech, and BIOS Laboratories) revealed a simple pattern of HFB4-1 hybridization, indicative of single copy or unique sequences. This sequence appears to be highly conserved, as hybridizing sequences were detected in all species tested.

Chromosomal mapping of HFB4-1 sequences was determined by somatic cell hybrid Southern blot analyses. Hybridization of HFB4-1 sequences to the DNA from a panel of human-hamster cell lines (BIOS Laboratories) showed mapping to human chromosome 4. Human osteonectin has been mapped to human chromosome 5, indicating that HP-8 is not encoded by the same gene as osteonectin, and also that the results of these southern analyses were not due to cross hybridization with human osteonectin sequences.

To circumvent the limitations of using a cDNA library to isolate 5' sequences from large mRNAs, a 5' RACE (Rapid Amplification of cDNA Ends) procedure was employed using a commercially available kit (Clontech, Palo Alto, Calif.). Using a 5' directed HFB4-1 (largest HP-8 containing cDNA clone)-specific antisense primer (HFB4-1-race-1A) and human brain poly-A RNA (Clontech, Palo Alto, Calif.) as template, an HP-8 specific 5' cDNA was synthesized to which a 5' "TAG" anchor primer sequence was ligated. Using a nested HP-8 antisense primer (HFB4-1-race-2A), and a "TAG" sequence sense primer, the HP-8 5' sequences were amplified by polymerase chain reaction (PCR). Subsequent "shotgun" litigation of the amplification product into the PCR2000 vector (TA cloning system, Invitrogen, San Diego, Calif.) and colony hybridization to another nested primer (HFB4-1-race-3A) allowed isolation of 5' HP-8 cDNA containing clones (RACE clones). DNA was purified from these candidates, and the inserts were characterized by restriction endonuclease (BAMHI or EcoRI) digestion, to release the insert, followed by size fractionation by agarose gel electrophoresis, transfer to nitrocellulose and subsequent Southern blot hybridization to HP-8 primer 3A (Sambrook, J., Fritsch, E. F., and Maniatis, T. (1989) *Molecular Cloning: a Laboratory Manual,* Second Edition, Cold Spring Harbor Laboratory Press, Cold Spring Harbor, N.Y.). Clones containing the largest "HFB4-1-race-3A" hybridizing inserts were subjected to DNA sequence analyses. Cycle sequencing (Applied Biosystems, Foster City, Calif.) of the inserts using polylinker primers and subsequent internal sequence specific primers (primer walking) was performed using an Applied Biosystems automated DNA sequencer. Sequences were edited using the Applied Biosystems SeqEd program and assembled using GEL software (Intelligenetics, Mountain View, Calif.). RACE clone #9 (TA-HB-RACE9) contained HP-8 cDNA sequence that overlapped with HFB4-1 sequences and encoded a continguous open reading frame (ORF). This clone is represented schematically in FIG. 1, and the sequence is included in FIGS. 2A-1 through 2A-8.

Because the sequence of RACE clone #9 did not contain the ATG start codon, the 5' RACE procedure was repeated, using primers designed to upstream sequences in RACE clone #9 (primers HFB4-1-race 4A and HFB4-1-race-5A), and screened with a RACE clone #9 upstream primer (HFB4-1-race-6S). One isolate, RACE clone #6 (TA-HB6) contained RACE clone #9 overlapping sequence, and encoded the putative ATG start codon, preceded by an in-frame stop codon. RACE clone #6 is depicted schematically in FIG. 1, and the sequence is included in FIGS. 2A-1 through 2A-8. The first 17 amino acids of the deduced sequence appear to encode a signal sequence characteristic of secreted proteins (Von Heijine, G. (1983) Eur. J. Biochem. 133:17). The predicted amino acid sequence shows some colinearity with the rat SC1 protein, but the percent identity is not as strong as in the "osteonectin domain", indicating that SC1 and HP-8 are two distinct and different proteins.

A multiple tissue northern blot was obtained from Clontech Laboratories, Palo Alto, Calif. (Catalog number: 7760-1) and hybridized to 32P labelled cDNA insert from HP-8. The probe was prepared according to manufacturers instructions (BRL, Gaithersburg, Md., Catalog number: 8187-SA) at high specific activity. Hybridization conditions were performed as described in the Clontech handbook for Product number 7760-1. Washed filters were air dried and exposed to XR-5 Kodak x-ray film for 18 hours at −70° C.

The epitope of the HP-8 antigen (i.e. SEQ ID NO:4) is about 60–80 percent homologous with various proteins and polypeptides which belong to the osteonectin family (see P. T. Russell et al., THE OSTEONECTIN FAMIL OF PROTEINS, J. Biochem., Vol. 20, No. 7, pp. 653–660, 1988). Specific examples of related osteonectin proteins are Osteonectin/BM401 SPARC and SC1. These specific osteonectins are described in the following three references:

1. J. H. McVey et al., CHARACTERIZATION OF THE MOUSE SPARC/OSTEONECTIN GENE, Jour. Biological Chem., Vol. 263, Issue of August 15, pp. 11111–11116, 1988;
2. J. Engel et al., CALCIUM BINDING DOMAINS AND CALCIUM-INDUCED CONFORMATIONAL TRANSITION OF SPARC/BM-40/OSTEONECTIN, AN EXTRACELLULAR GLYCOPROTEIN EXPRESSED IN MINERALIZED AND NONMINERALIZED TISSUE, Biochemistry, 1987, Vol. 26, 6958–6965; and
3. I. G. Johnston, et al., MOLECULAR CLONING OF SC1: A PUTATIVE BRAIN EXTRACELLULAR MATRIX GLYCOPROTEIN SHOWING PARTIAL SIMILARITY TO OSTEONECTIN/BM40/SPARC, Neuron, Vol. 2, 165–176, Jan. 1990.

The deduced amino acid sequence of HFB4-1 was used to search the PIR 38 and SWISS-Prot 26 databases using the FASTDB program (Intelligenetics). The deduced amino acid sequence of HFB4-1 showed an overall sequence identity of 62% with rat SC1, and 49% and 50% identity with human and murine osteonectin, respectively. The final 200 residues of the SC1 protein (634 aa), as derived from cDNA sequence shows approximately 65% sequence identity with the final 200 residues of osteonectin (304 aa). HFB4-1 amino acid sequence is also most similar to SC1 and to osteonectin/SPARC/BM40 throughout the C-terminal 200 residues.

DNA sequences which code on expression for HP-8 antigen may be inserted into appropriate expression vectors for expression in prokaryotic, eukaryotic or insect viral cells. A wide variety of expression vectors are available and may be used in conventional procedures to transform competent host cells for expression and isolation of the HP-8 antigen. Methods for preparing gene sequences, inserting the sequences into expression vectors, transforming competent hosts and growing the host in culture for production of products are disclosed in U.S. Pat. Nos. 4,710,473; 4,711, 843; and 4,713,339.

The HP-8 antigen can be used to generate antibodies. The HP-8 antigen can be used in any of the conventional procedures involving administering an antigen to a host animal in order to raise antibodies. The administration protocols, including dosage levels, administration schedules and isolation and recovery of antibodies from the host animal are all well known in the art. The HP-8 antigen is used in the same manner as any other antigen to elicit the production of antibodies in a host animal.

The HP-8 antigen includes epitopes which bind 3E10 antibodies and therefore will be useful in investigating the etiology of SLE. In addition, HP-8 will be useful in developing therapeutic rational drug designs which will be effective in treating SLE and other related connective tissue diseases such as rheumatoid arthritis.

All of the United States Patents, literature references and methodology handbooks set forth in this specification are hereby incorporated by reference.

Having thus described exemplary embodiments of the present invention, it will be understood by those skilled in the art that the above disclosures are exemplary only and that the present invention is not limited to the embodiments as disclosed herein, but is only limited by the following claims.

What is claimed is:

1. An isolated antigen having a molecular weight of from about 60 to 100 Kd, said antigen comprising a 44 amino acid epitope, said epitope having the amino acid sequence of SEQ. I.D. No. 4 and wherein said antigen is capable of binding 3E10 antibody.

2. An isolated antigen according to claim 1 wherein said antigen has the amino acid sequence of SEQ. I.D. No. 6.

3. A method for producing an antigen comprising the steps of:

providing a microorganism comprising a DNA sequence which, upon culturing, expresses an antigen having a molecular weight of from about 60 to 100 Kd, said antigen comprising a 44 amino acid epitope, said epitope having the amino acid sequence of SEQ. I.D. No. 4 and wherein said antigen is capable of binding 3E10 antibody;

culturing said microorganism in a nutrient medium for a sufficient length of time and under suitable conditions to form a mature cell culture which has expressed a recoverable amount of said antigen;

recovering said antigen from said mature cell culture to provide said antigen in a purified form.

4. A method for producing an antigen according to claim 3 wherein said antigen has the amino acid sequence of SEQ. I.D. No. 6.

\* \* \* \* \*